United States Patent [19]

Murphy et al.

[11] Patent Number: 5,202,505

[45] Date of Patent: Apr. 13, 1993

[54] PURIFICATION OF HYDROXYPHENYL ALKANES

[75] Inventors: Mark A. Murphy, Corpus Christi, Tex.; Mike R. Czarny, Charles City, Iowa

[73] Assignee: Hoechst Celanese Corporation, Del.

[21] Appl. No.: 858,383

[22] Filed: Mar. 24, 1992

[51] Int. Cl.$^5$ .............................................. C07C 37/68
[52] U.S. Cl. .................................. 568/756; 568/749; 568/750
[58] Field of Search ............... 568/717, 720, 724, 749, 568/748, 750, 756

[56] References Cited

U.S. PATENT DOCUMENTS 4,992,598  2/1991  Strutz et al. ........................ 568/720

FOREIGN PATENT DOCUMENTS 0115733   9/1981  Japan .................................. 568/724
0142936   9/1982  Japan .................................. 568/724
0159733  10/1982  Japan .................................. 568/724
2071090   9/1981  United Kingdom ................. 568/717

*Primary Examiner*—Werren B. Lone
*Attorney, Agent, or Firm*—James J. Mullen; Donald R. Cassady; Timothy L. Burgess

[57] ABSTRACT

Crude hydroxyphenylalkane, e.g., 1,1,1-tris(4'-hydroxyphenyl)ethane, is purified, to reduce color and prevent caustic solution turbidity, (a) by contacting the hydroxyphenylalkane in alcoholic solution with an alkali metal dithionite, preferably in the presence of an alkalinity agent such as an alkali metal borohydride, more preferably by introducing the dithionite into the alcoholic solution as an alkaline aqueous solution, (b) precipitating the hydroxyphenylalkane from the alcoholic solution, and optionally (c) rinsing the hydroxyphenylalkane with an alkaline aqueous solution of the dithionite.

19 Claims, No Drawings

PURIFICATION OF HYDROXYPHENYL ALKANES

BACKGROUND OF THE INVENTION

1. Field of the Invention

This invention relates to a method of purifying hydroxphenylalkanes, including tri(hydroxyphenyl)alkanes, such as 1,1,1-tris(4'-hydroxyphenyl) ethane (hereinafter identified for brevity as "THPE"), and more particularly, to methods which employ alkali metal dithionites in connection with such purification.

2. Description of Prior Art

THPE may be produced by reacting 4-hydroxyacetophenone with phenol. Typically, phenol is also used as the solvent. The reaction proceeds under acidic catalytic conditions, such as with a co-catalyst system of hydrochloric acid and beta-mercaptopropionic acid. The product contains substantial amounts of impurities which include mixtures of ortho and para tris(hydroxyphenol)ethane isomers, 1,1-bis(hydroxyphenyl)ethylene isomers, phenol, 4-hydroxyacetophenone, chlorides, and unidentified colored bodies and light and heavy ends. This crude reaction product is reddish-brown. A major application of THPE is use as a polycarbonate chainbranching agent. Color, transparency, and compound purity are extremely important in this application. Accordingly, the reaction product must by purified to isolate the THPE, and the THPE isolate must have low color and high transparency.

In U.S. Pat. No. 4,992,598, issued Feb. 12, 1991, assigned to the assignee of this invention, a process is described for purifying THPE resulting from the reaction of 4-hydroxyacetophenone with phenol. The process comprises:

(a) washing a crude product mixture of THPE and impurities resulting from the reaction, with a saturated solution of THPE in a solvent comprising from about 60% to 70% by weight of water and from about 25% to about 40% by weight of methanol;

(b) isolating the washed crude product mixture from the formed effluent washing composition, and dissolving the washed crude product mixture in methanol;

(c) optionally adding first sodium borohydride and then activated carbon to the washed crude mixture dissolved in methanol, and then filtering off the carbon;

(d) adding sufficient dilute aqueous sodium borohydride to the dissolved, washed crude mixture to form a precipitate of THPE;

(e) filtering the precipitate to form a purified THPE and filtrate;

(f) washing the filtered THPE precipitate with an aqueous methanol solution, which optionally contains THPE to saturation, and conducting the rinsing for a sufficient time to remove substantially all residual colored impurities from the precipitate; and (g) optionally rinsing the filtered precipitate with an aqueous solution of sodium dithionite.

Sodium dithionite is widely used as a bleaching agent. Oxygen should be excluded during all steps because aqueous $S_2O_4^{2-}$ is easily oxidized. Sodium borohydride is used extensively for the reduction of organic compounds. It has the ability to reduce aldehydes and ketones selectively in the presence of other functional groups, and, also, is useful in reducing carbonyl unsaturation, which can give rise to color. Notwithstanding use of sodium borohydride or sodium dithionite to advantageously reduce color in crude THPE cake according to the method of the above-described process, deeper color reduction is desirable.

SUMMARY OF THE INVENTION

Dissolution of THPE in caustic is a standard addition method for use with polycarbonates. Upon dissolution in caustic, sometimes THPE produced according to the method of the above-described U.S. Pat. No. 4,992,598 has had "haze" or "turbidity" in the solution. This turbidity was caused by the presence of small amounts of caustic insoluble sulfur or sulfur compounds, which would have originated with the sodium dithionite rinse solutions used for washing the final THPE product.

An object of this invention is to purify impure hydroxyphenylalkanes, including THPE.

An object of this invention is to provide a process for purifying impure hydroxyphenylalkanes, including THPE, in a way which minimizes or prevents turbidity of caustic solutions of hydroxyphenylalkanes, including THPE.

An object of this invention is to improve color in hydroxyphenylalkanes, including THPE, in a purification process.

In accordance with this invention, there is provided a process for the purification of hydroxyphenylalkanes from an impure mixture containing the hydroxyphenylalkane, which comprises dissolving such mixture in an alcohol to form an alcoholic hydroxyphenylalkane solution, adding an alkali metal dithionite to the alcoholic hydroxyphenylalkane solution, and then isolating the hydroxyphenylalkane from that solution.

In this process, the dithionite may be added to the alcoholic hydroxyphenylalkane solution, alternatively, (1) as a solid, (2) as an aqueous solution if added immediately after forming the aqueous solution, or (3) preferably in an alkaline aqueous premix solution. If the dithionite is added as a solid, preferably an alkali metal borohydride is added to the hydroxyphenylalkane alcoholic solution before the dithionite. If the dithionite is added as an alkaline aqueous premix solution, the alkaline solution consists essentially of the dithionite and an alkalinity agent preferably selected from the groups consisting of alkali metal borohydrides, hydroxides, carbonates and bicarbonates. Such alkaline aqueous premix solution is suitably formed by first adding the alkalinity agent, preferably the borohydride, and then the dithionite, to water. Such aqueous premix solution has an alkaline pH sufficiently higher than pH 7 that, when added to the alcoholic hydroxyphenylalkane solution, the resultant solution has an alkaline pH, preferably in the range from pH 7 to about 10.5, to inhibit dithionite decomposition. Preferably, dithionite is dissolved in an aqueous alkaline solution of an alkali metal borohydride, suitably formed by addition of the borohydride to an aqueous caustic solution, and the so-formed dithionite premix solution is added to the alcoholic hydroxyphenylalkane solution.

By conducting hydroxyphenylalkanes purification according to this invention, highly improved color reduction can be achieved.

Further, in accordance with our invention, after the hydroxyphenylalkane is isolated from solution, the isolated hydroxyphenylalkane is washed with an aqueous alkaline wash solution containing (i) a minor proportion of an aliphatic $C_1$–$C_4$ alcohol, (ii) a major proportion of water, (iii) an alkali metal dithionite, and (iv) sufficient caustic for the aqueous alkaline wash solution to have a pH in a range from about 7 to about 10.5. The aqueous alkaline wash solution is formed with the caustic before the alkali metal dithionite is added.

By washing the isolated hydroxyphenylalkane with the alkaline aqueous alcoholic wash solution containing the dithionite, turbidity from caustic insoluble impurities in the purified hydroxyphenylalkane product is minimized or eliminated.

Suitably, the alcohol in which the hydroxyphenylalkane is dissolved to form an alcoholic solution is a aliphatic $C_1$–$C_4$ alcohol, preferably methanol. Suitably, the same alcohol is used in the aqueous wash solution for the isolated hydroxyphenylalkane.

Alkali metal, when used in this invention, refers to lithium, sodium or potassium. Preferably, the alkali metal borohydride is sodium or potassium borohydride, and the alkali metal dithionite is sodium or potassium dithionite.

The pH of the alkaline aqueous alcoholic hydroxyphenylalkane solution resulting from addition of the premix solution of the dithionite and alkalinity agent preferably is in the range from pH 7 to pH 10.5, for at a pH between about 9.5 and 10.5, deprotonation of phenolic hydroxyl groups begins. This is undesirable unless the alkali metal salts of hydroxyphenylalkane are wanted. Accordingly, pH of the resulting solution preferably is below 10.5, and more preferably below 9.5. Operationally, it is desirable to cause isolation of the hydroxyphenylalkane as a solid using filtration or centrifugation at about pH 7. Slight modification of pH can be done prior to centrifugation.

Also, suitably, the alcoholic hydroxyphenylalkane is clarified by contacting it with activated particulate carbon and then separating it from the particulate carbon, preferably before the alkali metal dithionite is added to the alcoholic hydroxyphenylalkane solution.

Hydroxyphenylalkanes which suitably may be purified by the method of this invention are represented by the formula:

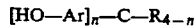

$$[HO-Ar]_n-C-R_{4-n}$$

in which (i) Ar represents an aromatic phenyl radical substituted at the ortho and/or para position, or a naphthyl radical, substituted at one or more of the 1, 3, 6, and 7, positions, the substitution being by hydroxyl groups represented in the formula by OH, (ii) n is an integer from 1 to 3, and (iii) R is hydrogen or a $C_1$–$C_8$ branched or unbranched alkyl or cycloalkyl group. Thus, hydrophenylalkanes which are comprehended suitably include mono-, di-, or tri-(hydroxyphenyl)alkanes, for example, mono-, di- and tri-(hydroxyphenyl)ethane, mono-, di-, and tri-(hydroxyphenyl)propane, mono-, di-, and tri-(hydroxyphenyl)butane, mono-, di-and tri-(hydroxyindane)ethane, and preferably include 1,1,1-tris(4'-hydroxyphenyl)ethane, herein called THPE, with respect to which the preferred embodiment is described.

DETAILED DESCRIPTION OF THE PREFERRED EMBODIMENT

The production of THPE may be performed by the reaction of 4-hydroxyacetophenone and phenol. Phenol is the solvent, as well as the reagent. The reaction takes place in a reactor with hydrochloric acid and betamercaptopropionic acid as preferred co-catalysts. The resulting reaction product contains THPE and a significant amount of impurities, which include those impurities mentioned above under the description of the prior art.

In the first step of the purification method, a crude mixture or cake recovered from the reactor where THPE is formed is washed, suitably at about 10°–50° C., preferably about 25° C., with an alcoholic solution comprising from about 60% to about 100% by weight water and from about 0% to about 40% by weight of methanol. Suitably, from about 10% to about 40%, preferably, about 34%, of aqueous methanol solution is used. This washing suitably is conducted in a number of repetitious washing steps. The inclusion of THPE saturated mother liquor from a previous crystallization in the washing step reduces the amount of THPE lost into the washing solution from the crude cake, as disclosed in U.S. Pat. No. 4,992,598. Suitably, the washing operation may be conducted by slurrying, filtering, and refiltering. Preferably, the contents of the reaction tank where THPE was produced are transferred into a filtration separator to separate the crude cake from the mother liquor. The aqueous methanol wash solution is then passed through the filter, collected, and recycled a plurality of times. Suitably, in addition, from about 0.01 to about 1.0 weight percent of sodium hydrosulfite (sodium dithionite) may be added to the recycle wash solution.

After washing, the crude cake remains on the filter. An alcoholic solvent, suitably an aliphatic $C_1$–$C_4$ alcohol, preferably methanol, suitably at a temperature of from about 20° C. to about 60° C., preferably about 50° C., is then circulated and recirculated through the filter to dissolve the THPE into an alcoholic THPE solution.

Suitably, the alcoholic THPE solution is then clarified using particulate activated carbon. Particulate activated carbon is charged to a carbon slurry tank and mixed with water, and the slurry is then cycled through a filter to precoat the filter. Then, the alcoholic THPE solution is cycled and recycled a number of times through the filter to contact the solution with the carbon coated on the filter support.

Next, the clarified alcoholic THPE solution is passed to a reactor. An alkaline aqueous solution of sodium borohydride, suitably, a 12 weight percent solution in 14 molar caustic, is charged to water in a nitrogen flushed preparation tank and sodium dithionite is then added to the water to form a solution having concentrations in the ranges described in the next following paragraph. The resulting solution is well mixed and then rapidly transferred to the reactor containing the alcoholic THPE solution. An agitator in the reactor is turned on and the reactor is charged with deionized water, suitably at a temperature of about 10° to 50° C., preferably about 25° C., in quantity sufficient for a time sufficient to precipitate the THPE out of solution.

Suitably, the sodium dithionite employed in the treating solution for the alcoholic THPE solution is present in an amount from about 0.01 to about 1.0 weight percent of the aqueous treating solution, more preferably, from about 0.05 to about 0.5 weight percent and, most preferably, about 0.15 weight percent. Suitably, from about 0.0003 to about 0.3 weight percent of sodium borohydride, more preferably, from about 0.003 to about 0.07 weight percent, still more preferably from about 0.01 to about 0.03 weight percent, and most preferably, about 0.02 weight percent is employed in the treating solution, with the weight ratio of sodium borohydride to sodium dithionite suitably being from about 3:1 to about 12:1, more preferably, from about 5:1 to about 10:1, most preferably, about 7:1. Preferably, the sodium dithionite is added to the already alkaline aqueous borohydride solution, as described, for best results.

As more fully detailed in examples that follow, it is possible within the scope of the invention to obtain THPE color reduction by adding an aqueous solution of sodium dithionite directly to the alcoholic THPE solution; however, it is imperative that the sodium dithionite be added to the alcoholic THPE solution immediately upon having been formed, for the dithionite solution loses color reducing effectiveness with aging. The rate of this reduction in effectiveness significantly depends on acidity of the pH. In the preferred embodiment, the dithionite is stabilized with an alkalinity agent.

In accordance with this invention and as illustrated in examples below, suitable results are obtained by adding sodium borohydride and sodium dithionite as solids directly to the alcoholic THPE solution, more preferably, by first adding the soddium borohydride with agitation, followed by addition of the sodium dithionite. Alternatively, the sodium borohydride may be mixed with sodium dithionite in water, and the aqueous solution added to the alcoholic THPE solution. If this is done, the sodium borohydride preferably is added first to cause this solution to be alkaline before the sodium dithionite is added. At acidic or neutral pH, borohydrides decompose by hydrolysis in water and in methanol, and to a lesser extent in ethanol (sodium borohydride is stable in 2-propanol and t-butanol). In the absence of acid, the hydrolysis after a short time increases the pH of the solution. Thus, in this context, the borohydride in this invention serves as an alkalinity producing agent in water or in methanol or ethanol to which sodium dithionite has not been added. When solid sodium dithionite is dissolved in water, acidic solutions with a pH in the range from about 3 to 4 result, both from impurities in the dithionite and from air oxidation and hydrolysis. By adding the borohydride to water, methanol, or ethanol, sufficiently in advance of adding dithionite, the borohydride can elevate the pH to at least a slightly basic pH and stabilize solid sodium dithionite added to the solution. Sodium or potassium hydroxide may be used in lieu of sodium borohydride for alkaline aqueous solutions prepared from solid sodium dithionite. As mentioned, however, the more preferred embodiment employs sodium borohydride itself stabilized in an aqueous solution of caustic, for example, in 14 molar (40 weight percent) sodium hydroxide in water.

After precipitation of the THPE is complete, the precipitated THPE is separated from the liquid phase, suitably by pumping the slurry of THPE precipitate and aqueous liquid through a filter or centrifuge, spinning the cake dry in the centrifuge, and collecting the dry cake in the centrifuge basket.

In an aspect of this invention, the isolated THPE in a centrifuge basket is washed with an aqueous alkaline wash solution comprising a minor proportion of an aliphatic $C_1$–$C_4$ alcohol, preferably methanol, an alkali metal dithionite, preferably sodium dithionite, a major proportion of water, and caustic sufficient for the solution to have a pH in the range from about 7 to about 10.5, preferably from about 8 to about 9.5. Suitably, the wash solution contains from about 0% to about 45% by weight of methanol, from about 0.01 to about 1.0 weight percent based on the solution, of sodium dithionite, more preferably, from about 0.05 to 0.50 weight percent, most preferably, about 0.15 weight percent sodium dithionite, and from about 0.01 to about 0.1 weight percent, based on the solution, of sodium hydroxide, with the balance being water.

After each basket is washed with the alkaline aqueous alcohol wash solution of dithionite, the purified THPE cake is then spun dry, collected and dried under vacuum.

The invention is illustrated by the following examples. These are to be understood only as illustrating embodiments of the invention and not therefore as limiting its scope, for the invention admits of other equally effective embodiments within the scope of the appended claims.

In the examples which follow, most of the tests were carried out in standard laboratory glassware. Because of slow air oxidation of sodium dithionite solutions, reasonable but not rigorous precautions were taken to conduct the experiments under $N_2$ atmosphere. For instance, solutions containing dithionite were prepared by dissolving $Na_2S_2O_4$ in degassed water, but were sometimes rapidly poured through air into a $N_2$ purged glass vessel. Filtrations were carried out in a $N_2$ purged glovebag. The wet solids resulting from filtrations were generally dried overnight in vacuum ovens at 60° C., and then analyzed by HPLC and for color, sulfur, and sodium.

EXAMPLE 1

Tests 1–4 included four separate THPE recrystallizations. A sample of high color THPE produced according to the method of U.S. Pat. No. 4,992,598 was used as starting material (it originally had measured 214 APHA color units, 0.08% total light ends, and 0.23% total heavy ends). Forty gram samples of the THPE were dissolved in 100 gr of methanol (hereinafter "MeOH"), and 0.040 gr of $NaBH_4$ was added under $N_2$ inside a stirred three-necked flask. Degassed water (200 gr) for precipitation of the THPE was prepared according to the following schedule, containing the indicated additives.

| Test | Additives to 200 gr of $H_2O$ |
|---|---|
| 1 | None |
| 2 | 0.040 gr $NaBH_4$ |
| 3 | 0.28 gr $Na_2S_2O_4$ |
| 4 | 0.040 gr $NaBH_4$, 0.28 gr $Na_2S_2O_4$ |

The water was added to a dropping funnel on the flask containing the THPE/MeOH, and slowly added over the period of about 1 hour to precipitate the THPE. The precipitated THPE was filtered on a Buchner funnel inside a $N_2$ purged glovebag, washed with 100 gr of deionized water, then dried overnight in a vacuum oven at 60° C. Samples were submitted for analysis by HPLC and for color, sulfur, and sodium analysis. The results are shown in Table I.

Referring to Table I, a small color reduction (−21 APHA units) was observed by recrystallization in the absence of both borohydride and dithionite. A larger color reduction (−68 units) was obtained in the presence of only borohydride, while very little (−8 units) was obtained in the presence of only dithionite (this result was probably highly time dependent, see tests 9, 10 below). Surprisingly, a large color improvement (−167 units) was observed in the presence of the combination of borohydride and dithionite.

EXAMPLE 2

Tests 5-8 were identical to tests 1-4, except that no NaBH₄ was added to the MeOH used to dissolve the THPE. The additives to the water used for precipitation were:

| Test | Additives to 200 gr of H₂O |
|---|---|
| 5 | None |
| 6 | 0.040 GR NaBH₄ |
| 7 | 0.28 gr Na₂S₂O₄ |
| 8 | 0.040 gr NaBH₄, 0.28 gr Na₂S₂O₄ |

The results of tests 5-8 are set forth in Table I.

Referring to Table I, the absence of both additives actually produced a large color increase (+172 units) for unexplained reasons. Addition of only borohydride again produced a small color reduction (−68 units), while addition of only dithionite increased color by +47 units (this may have been a time dependent experimental artifact, see tests 9 and 10 below). Surprisingly again, addition of both borohydride and dithionite in the water used for precipitation produced a large color improvement (−158 units).

EXAMPLE 3

These tests were to test the effect of time on the effectiveness of unbuffered Na₂S₂O₄ solutions for decreasing color in the THPE recrystallization. Both experiments duplicated test 7, except that in test 9, the addition of unbuffered Na₂S₂O₄ to MeOH began immediately after the Na₂S₂O₄/H₂O was mixed, while in test 10 the Na₂S₂O₄ solution was allowed to stand for 30 minutes before addition to the THPE/MeOH was begun. These results are in Table I. The results indicate an unbuffered aqueous Na₂S₂O₄ solution loses effectiveness to reduce color as it ages before use.

EXAMPLE 4

Tests 11-14 were identical to tests 5-8, except that NaOH instead of NaBH₄ was added to the water used to precipitate the THPE, and Na₂S₂O₄ solution was added to the THPE/MeOH solution as in test 9. The additives to the water used for precipitation were:

| Test | Additives to 200 gr of H₂O |
|---|---|
| 11 | None |
| 12 | 0.041 gr NaOH |
| 13 | 0.28 gr Na₂S₂O₄ (addition to MeOH started immediately as in test 9) |
| 14 | 0.041 gr NaOH, 0.28 gr Na₂S₂O₄ |

After addition of the NaOH to the water, the pH was 11.8-11.9. Addition of the Na₂S₂O₄ lowered the pH to 9.87. The results of tests are set forth in Table I.

Referring to Table I, absence of either hydroxide or dithionite increased color by 82 units. Presence of hydroxide increased color by 37 units. Presence of dithionite (added more quickly than in previous experiments) decreased color by a large −203 units, while the combination of hydroxide and dithionite decreased color by −173 units.

TABLE I

| Example No. | Test No. | Additives | Color (apha) | Sulfur (ppm) | Sodium (ppm) |
|---|---|---|---|---|---|
| 1 | Sample | | 288,250 | | |
| A | 1 | None | 267 | 78 | <1 |
| | 2 | NaBH₄ | 220 | 52 | <1 |
| | 3 | Na₂S₂O₄ | 280 | 35 | 32 |
| | 4 | NaBH₄ + Na₂S₂O₄ | 121 | 17 | 7 |
| 2 | 5 | None | 460 | 70 | 12 |
| | 6 | NaBH₄ | 220 | 52 | <1 |
| | 7 | Na₂S₂O₄ | 335 | 61 | <1 |
| | 8 | NaBH₄ + Na₂S₂O₄ | 130 | 35 | <1 |
| 3 | 9 | Na₂S₂O₄ | 177 | <1 | |
| | 10 | Na₂S₂O₄ | 227 | <1 | |
| 4 | 11 | None | 370 | 44 | <1 |
| | 12 | NaOH | 325 | 35 | <1 |
| | 13 | Na₂S₂O₄ | 85 | 26 | <1 |
| | 14 | NaBH₄ + Na₂S₂O₄ | 115 | 17 | <1 |

EXAMPLE 5

In tests 15-18, the general procedure of tests 8 and 14 were employed for a larger scale laboratory recrystallization, but rather than adding the alkaline aqueous solutions of Na₂S₂O₄/alkalinity agent immediately to the solution of THPE dissolved in MeOH, the alkaline aqueous solution was aged. In tests 15-16, the alkalinity agent was NaBH₄; in tests 17-18, the agent was NaOH.

More particularly, in tests 15-16, 400 gr of THPE from another THPE sample (color=240 APHA units) produced by the method of U.S. Pat. No. 4,992,598 was dissolved in 1 liter of MeOH. 0.30 grams of NaBH₄ were added to 3.0 liters of deionized water to give a solution of pH=9.76. Addition of 2.8 grams of Na₂S₂O₄ gave a solution of pH=8.78, which was allowed to stand for 30 minutes, then was slowly added to the THPE/MeOH solution over 1 hour to precipitate the THPE. The precipitated THPE was filtered, and the filtrate pH equaled 8.78. One half of the solid THPE was collected for sampling (test 15), while the other half was washed with 4×125 ml of deionized water (test 16).

In tests 17-18, 400 gr of THPE from a different THPE sample (color=475 APHA units) produced by the method of U.S. Pat. No. 4,992,598 was dissolved in 1 liter of MeOH. 0.40 grams of NaOH were added to 3.0 liters of deionized solution to give a solution of pH=11.50. Addition of 2.8 grams of Na₂S₂O₄ gave a solution of pH=9.79, which was allowed to stand for 30 minutes, then added to the THPE/MeOH over 1 hour. The precipitated THPE was filtered, and the filtrate pH equaled 9.28. One half of the solid THPE was collected for sampling (test 17), while the other half was washed with 4×125 ml of deionized water (test 18).

The results of tests 15-18 are set forth in Table II. Both recrystallized THPE samples 15 and 16 showed a large color reduction, to 76 and 82, respectively. The water wash (test 16) had little affect on color, but did effect sodium and sulfur levels.

In tests 17-18, there was significant color reduction (to about 290 APHA).

EXAMPLE 6

Small scale tests were run in an attempt to reproduce the decolorization results of tests 17 and 18. Test 19 used a combination of NaBH₄ and Na₂S₂O₄ in a procedure essentially equivalent to test 8. Test 20 used a combination of NaOH and Na₂S₂O₄ in a procedure essentially equivalent to test 14, except that addition of the water solution to the MeOH/THPE was delayed for 30 minutes after mixing of the $Na_2S_2O_4$ and water. Test 21 used a combination of NaOH and $Na_2S_2O_4$ in a procedure equivalent to test 14. The results are set forth in Table II.

TABLE II

| Example No. | Test No. | Additives | Color (apha) | Sulfur (ppm) | Sodium (ppm) |
|---|---|---|---|---|---|
| 5 | Sample B | | 240 | | |
| | 15 | $NaBH_4 + Na_2S_2O_4$ | 76 | 56 | 32 |
| | 16 | $NaBH_4 + Na_2S_2O_4$ | 82 | <1 | 7 |
| | Sample C | | 475 | | |
| | 17 | $NaOH + Na_2S_2O_4$ | 290 | 79 | |
| | 18 | $NaOH + Na_2S_2O_4$ | 282 | <1 | |
| 6 | Sample D | | 285 | | |
| | 19 | $NaBH_4 + Na_2S_2O_4$ | 208 | <1 | |
| | 20 | $NaOH + Na_2S_2O_4$ | 188 | <1 | |
| | 21 | $NaOH + Na_2S_2O_4$ | 220 | 150 | |

EXAMPLE 7

These experiments used actual samples of production crude THPE, as MeOH solutions, for recrystallization experiments. MeOH was used to dissolve crude washed product cake, which was then carbon treated, giving a light amber solution which contained about 30% THPE. See U.S. Pat. No. 4,992,598.

In the typical procedure used in the tests, 280 grams of the amber solution mentioned above was placed in 1 liter, 3-neck roundbottom flasks with stirbars, which were fitted with addition funnels and purged with $N_2$. 400 grams of water was added to the MeOH/THPE over about one hour to precipitate THPE. The product THPE was filtered inside an $N_2$ purged glovebag, washed with 4×50 ml of deionized water, and then transferred to a vacuum oven for overnight drying at 60° C. The resulting samples were analyzed by HPLC, for color, and for sulfur by microcoulometry.

Tests 22-25 examined the use of dithionite and borohydride separately, and together, by addition of the solids to the methanol solution of THPE, before addition of water, as follows:

| Test | Additives |
|---|---|
| 22 | No additives were used |
| 23 | 0.060 grams of $NaBH_4$ was added to the MeOH solution and stirred 15 minutes before the precipitation |
| 24 | 0.56 grams of $Na_2S_2O_4$ was added to the MeOH and stirred for 30 minutes prior to the precipitation |
| 25 | 0.060 grams of $NaBH_4$ was added to the MeOH solution and stirred 5 minutes. 0.56 grams of $Na_2S_2O_4$ was then added to the MeOH and stirred 10 minutes. Precipitation was then begun. |

The results are set forth in Table III. Both borohydride and dithionite individually showed some color improvement, but the combination (test 25) showed the largest and best improvement, to a color of 215.

EXAMPLE 8

Tests 26-29 repeated the general procedure of Example 7, but added the borohydride or dithionite or both to the water, rather than the methanol, as follows:

| Test | Additives |
|---|---|
| 26 | No additives were used |
| 27 | 0.060 grams of $NaBH_4$ was added to water in the addition funnel, then precipitation began immediately |
| 28 | 0.56 grams of $Na_2S_2O_4$ was added to water in the addition funnel, then precipitation begun immediately |
| 29 | 0.060 grams of $NaBH_4$ was added to water in the addition funnel, then 0.56 grams of $Na_2S_2O_4$ was also added to the addition funnel precipitation begun. |

The results are set forth in Table III. Some color reduction was achieved (a best of 380, by the combination of dithionite and borohydride), but significantly less than when they were added to the methanol.

EXAMPLE 9

In test 30, sodium borohydride was added to the water in the form of a commercially available 12 wt % solution in 14M caustic, then sodium dithionite was added to the water, then the aqueous $NaBH_4/Na_2S_2O_4$ solution was added to the MeOH/THPE. In test 31, the caustic borohydride was used alone. Test 32 is the same as test 31, except pH was reduced to 10.11 with HCl before precipitation of THPE was begun. Thus:

| Test | Additives |
|---|---|
| 30 | 0.50 grams of commercial 12 wt % $NaBH_4$ in 14M NaOH (~0.060 grams $NaBH_4$) was added to the water, then 0.56 grams of $Na_2S_2O_4$ was also added to the water, and mixed under $N_2$ for 1 hour. Precipitation of THPE was then begun. |
| 31 | Same as 30, but no $Na_2S_2O_4$ was added |
| 32 | Same as 31, but pH of $NaBH_4/NaOH/H_2O$ was adjusted to 10.11 with 1:4 $HCl/H_2O$ before precipitation of THPE |

The results are set forth in Table III. As seen from Table III, with test 30, when the alkaline aqueous sodium dithionite solution is formed by adding it to a solution of sodium borohydride in aqueous caustic, a remarkable color reduction was achieved. Test 31 shows that addition of only the caustic solution of sodium borohydride gave poorer color reduction. Test 32 shows better results with the solution of test 31 are achieved at pH's less than 10.5.

TABLE III

| Example No. | Test No. | Additives | Color (apha) | Sulfur (ppm) |
|---|---|---|---|---|
| 7 | 22 | None | 1008 | 89 |
| | 23 | Solid $NaBH_4$ | 405 | 112 |
| | 24 | Solid $Na_2S_2O_4$ | 528 | 165 |
| | 25 | $NaBH_4 + Na_2S_2O_4$ (solids) | 215 | 161 |
| 8 | 26 | None ($H_2O$) | >500 | 123 |
| | 27 | Solid $NaBH_4$ | >500 | 101 |
| | 28 | Solid $Na_2S_2O_4$ | >500 | 98 |
| | 29 | $NaBH_4 + Na_2S_2O_4$ | 380 | 377 |
| 9 | 30 | $NaBH_4/NaOH + Na_2S_2O_4$ | 101 | 96 |
| | 31 | $NaBH4/NaOH$ | 417 | 87 |
| | 32 | $NaBH_4/NaOH$ (+pH adj) | 306 | 244 |

EXAMPLE 10

Laboratory deionized water had a pH of 5.6. Sodium dithionite 0.14 gr) was added to 100 ml of this water, and the pH measured immediately at 3.78. It turned visibly hazy within 5 minutes, and extremely hazy within 10 minutes. Turbidity of this solution was measured at reasonable intervals (after shaking and sampling the solutions) as indicated below, using a Hach ratio turbidimeter.

| Time (hours) | Turbidity (NTU) |
| --- | --- |
| ~0 | 0.2 |
| ~0.08 | >200 |
| ~0.15 | 545 |
| 0.5 | 440 |
| 2.5 | 304 |
| 3.5 | 280 |
| 4.5 | 192 |
| 20.5 | 0.60 |

A second, similar solution was prepared, which consisted of 500 cc of water, 0.194 grams of 50% sodium hydroxide solution, and 0.700 grams of sodium dithionite. The caustic buffered dithionite solution had a pH of 9.10, and remained completely clear over the same time period as above, with periodic turbidity measurements showing consistent turbidities of ~0.02 NTU.

When THPE was washed on a Buchner funnel with unbuffered, hazy solutions of sodium dithionite, the THPE essentially acted as a filter, completely removing the haziness from the water. Oven drying of the solid THPE, dissolution in caustic, and measurement of its turbidity showed large increases in turbidity.

In summary—unlike in the method described in U.S. Pat. No. 4,992,598, where aqueous sodium dithionite was employed only to rinse solid THPE—in this invention, as shown by the examples, unexpectedly high color reduction and little or no caustic solution turbidity is achieved from crude hydroxyphenyl alkanes purified by alkali metal dithionite treatment of the hydroxyphenylalkane in solution, preferably alkaline solution, and, optionally, by rinse later with dithionite in an aqueous alkaline solution when the hydroxyphenylalkane is a solid.

Having described and illustrated the invention, it will be appreciated by those skilled in the art that the invention admits of other embodiments within the scope of the claims.

What is claimed is:

1. A process for the purification of an hydroxyphenylalkane from an impure mixture containing an hydroxyphenylalkane, comprising:
    a) dissolving said mixture in an alcohol to form an alcoholic hydroxyphenylalkane solution,
    b) adding an alkaline aqueous solution consisting essentially of an alkali metal dithionite and an alkalinity agent in water to said hydroxyphenylalkane solution, and
    c) isolating said hydroxyphenylalkane from said solution of step (b).

2. The process of claim 1 in which said alkalinity agent is selected from the group consisting of alkali metal borohydrides, hydroxides, carbonates or bicarbonates.

3. The process of claim 2 in which said alkalinity agent is a said borohydride.

4. The process of claim 2 in which said alkalinity agent is a said hydroxide.

5. The process of claim 3 in which said alkaline aqueous solution is formed by adding first said borohydride then said dithionite to water.

6. The process of claim 1 in which said alkaline aqueous alcoholic solution in step (b) has a pH in the range from 7 to 10.5.

7. The process of claim 3 in which said alkaline aqueous solution of an alkali metal borohydride consists essentially of said borohydride in aqueous caustic.

8. The process of claim 1 in which said hydroxyphenylalkane is recovered as a precipitate, and further comprising washing said hydroxyphenylalkane with an alkaline aqueous washing solution comprising a minor proportion of an aliphatic $C_1$–$C_4$ alcohol, a major proportion of water, an alkali metal dithionite and sufficient caustic for said washing solution to have a pH in the range from about 7 to about 10.5.

9. The process of claim 8 in which said dithionite is added after said caustic in the formation of said alkaline aqueous solution.

10. A process for the purification of 1,1,1-tris(4'-hydroxyphenyl)ethane ("THPE") from a substantially crude cake containing THPE and impurities resulting from the production of THPE from 4-hydroxyacetophenone and phenol, comprising,
    (a) washing said crude cake with a saturated solution of THPE in solvent comprising from about 60% to about 100% by weight water and from about 0% to about 40% by weight of an aliphatic $C_1$–$C_4$ alcohol;
    (b) separating the washed cake from the effluent composition formed by said washing step (a);
    (c) dissolving the washed cake from step (b) in an aliphatic $C_1$–$C_4$ alcohol to form an alcoholic solution containing THPE;
    (d) adding to said alcoholic solution an alkaline aqueous solution consisting essentially of an alkali metal borohydride and an alkali metal dithionite in water to form a treated solution; and
    (e) precipitating THPE from said treated solution to recover purified THPE.

11. The process of claim 10 in which said alkaline aqueous solution is formed by adding first said borohydride then said dithionite to water.

12. The process of claim 11 in which said treated solution of step (d) has a pH in the range from 7 to 10.5.

13. The process of claim 10 in which said alkaline aqueous solution is formed by adding said dithionite to an alkaline aqueous solution of said borohydride.

14. The process of claim 13 in which said alkaline aqueous solution of said borohydride consists essentially of said borohydride in aqueous caustic.

15. The process of claim 10 in which said THPE is recovered as a precipitate, and further comprising washing said recrystallized THPE with an aqueous alkaline washing solution comprising a minor proportion of an aliphatic $C_1$–$C_4$ alcohol, a major proportion of water, an alkali metal dithionite and sufficient caustic for said washing solution to have a pH in the range from about 7 to about 10.5.

16. The process of claim 10 further comprising contacting the solution from step (c) with particulate activated carbon to clarify the solution, followed by isolating the clarified solution from said carbon, then performing step (d) on said clarified solution.

17. A process for treating THPE produced by reaction of 4-hydroxyacetophenone with phenol and purified in a process including precipitating purified THPE from an alcoholic solution of the crude THPE, which comprises washing said purified THPE crystals with alkaline aqueous alcoholic wash solution of an alkali metal dithionite having a pH not exceeding about 10.5.

18. The process of claim 17 in which said alkaline aqueous alcoholic wash solution comprises from about 60% to about 100% by weight water, from about 0% to about 40% by weight methanol, from about 0.01 to about 1.0 weight percent on said water of sodium dithionite, and from about 0.01 to about 0.1 weight percent on said water of sodium or potassium hydroxide, and wherein said dithionite is added after said hydroxide.

19. A process for the purification of 1,1,1-tris(4'-hydroxyphenyl)ethane ("THPE") from a substantially crude cake containing THPE and impurities resulting from the production of THPE from 4-hydroxyacetophenone and phenol, comprising,
  (a) washing said crude cake with a saturated solution of THPE in solvent comprising from about 60 to about 100% by weight water and from about 0% to about 40% by weight methanol;
  (b) separating the washed cake from the effluent composition formed by said washing step (a);
  (c) dissolving the washed cake from step (b) in methanol to form a methanolic solution containing THPE;
  (d) contacting the methanolic solution from step (c) with particulate activated carbon to produce a clarified methanolic solution containing THPE;
  (e) adding to said clarified methanolic THPE solution an alkaline aqueous premix solution formed by adding sodium dithionite to a solution of sodium borohydride in aqueous caustic, said formed solution comprising from about 0.0003 to about 0.3 weight percent on water of sodium borohydride and from about 0.01 to about 1.0 weight percent sodium dithionite, to provide an alkaline aqueous alcoholic solution having an alkaline pH less than pH 10.5;
  (f) either as step (e) or as a separate succeeding step adding sufficient water to said clarified methanolic THPE solution to form a THPE precipitate;
  (g) recovering said precipitate of THPE; and
  (h) washing said precipitate of THPE with an alkaline aqueous wash solution comprising from about 60% to about 100% by weight water, from about 0% to about 40% by weight methanol, and from about 0.01 to about 1.0% by weight sodium dithionite, such alkaline wash solution having a pH less than about 10.5.

* * * * *